(12) United States Patent
Walpole et al.

(10) Patent No.: US 10,478,588 B2
(45) Date of Patent: Nov. 19, 2019

(54) THERAPEUTIC FIELD GENERATOR DEVICE AND METHOD

(71) Applicant: ZEEZ TECHNOLOGY LTD, London (GB)

(72) Inventors: Stephen John Walpole, Harleston (GB); Anna Sophia McKay, London (GB)

(73) Assignee: ZEEZ TECHNOLOGY LTD, London (GB)

( * ) Notice: Subject to any disclaimer, the term of this patent is extended or adjusted under 35 U.S.C. 154(b) by 65 days.

(21) Appl. No.: 15/303,346

(22) PCT Filed: Apr. 10, 2015

(86) PCT No.: PCT/GB2015/051102
§ 371 (c)(1),
(2) Date: Oct. 11, 2016

(87) PCT Pub. No.: WO2015/155545
PCT Pub. Date: Oct. 15, 2015

(65) Prior Publication Data
US 2017/0028166 A1    Feb. 2, 2017

(30) Foreign Application Priority Data
Apr. 11, 2014    (GB) .................... 1406604.7

(51) Int. Cl.
*A61M 21/02* (2006.01)
*A61N 2/02* (2006.01)
(Continued)

(52) U.S. Cl.
CPC ............. *A61M 21/02* (2013.01); *A61N 2/004* (2013.01); *A61N 2/02* (2013.01); *A61M 2021/0055* (2013.01)

(58) Field of Classification Search
CPC ......... A61N 2/004; A61N 2/02; A61M 21/02; A61M 2021/0055
(Continued)

(56) References Cited

U.S. PATENT DOCUMENTS 5,314,401 A * 5/1994 Tepper ..................... A61N 2/02
                                                              600/14
6,029,084 A * 2/2000 Long ........................ A61N 1/40
                                                              607/2
(Continued)

FOREIGN PATENT DOCUMENTS

DE          20004092 U1    3/2000
EP          0390844 A1    10/1999
(Continued)

OTHER PUBLICATIONS

International Preliminary Report on Patentability dated Oct. 12, 2016 in PCT/GB2015/051102.
(Continued)

*Primary Examiner* — Navin Natnithithadha
*Assistant Examiner* — Sunita Reddy
(74) *Attorney, Agent, or Firm* — Young Law Firm, P.C.

(57) ABSTRACT

A portable therapeutic field generator device (10) generates a reduced magnetic field component for a relatively large electric field by virtue that adjacent conductive tracks in a radiating element (40, 50) conduct electrical current in opposing directions. The device (10) includes a processor (12) that, in response to a control algorithm stored in memory (14), supplies a pulse wave (22) to a circuit containing the radiating element (40, 50). The pulse establishes generation of a base heartbeat reference having a frequency around a nominal heart rate. At periodic times, the base heart beat reference is supplemented by mutually exclusive periods of alpha wave, theta wave and delta wave
(Continued)

generation (or other selected frequencies below about 200 Hz) based on selected brainwave frequencies for these waves, with the pulses having a duration generally corresponding to that ascribed to neuron depolarisation pulses. The device (10) cycles through multiple cycles (88) and, dependent upon the effect that is desired, may see delta wave frequencies follow theta wave frequencies that follow alpha wave frequencies. Delays may exist between transitions between the generated waves, with delta wave generation occurring no later than sixty minutes from commencement of alpha wave production for a mode that induces sleep. Delta waves production has, typically, a duration that is twice that of either the alpha or theta wave production. A second mode of operation sees longer pulse times for higher frequencies—between about 100 Hz and 500 Hz—associated with muscle stimulation.

15 Claims, 4 Drawing Sheets

(51) Int. Cl.
    *A61N 2/00*     (2006.01)
    *A61M 21/00*     (2006.01)

(58) Field of Classification Search
    USPC .......................................... 600/9–15
    See application file for complete search history.

(56) References Cited

U.S. PATENT DOCUMENTS

| | | | | |
|---|---|---|---|---|
| 6,132,362 | A * | 10/2000 | Tepper | A61N 2/02 600/14 |
| 6,261,221 | B1 * | 7/2001 | Tepper | A61N 2/02 600/13 |
| 6,418,345 | B1 * | 7/2002 | Tepper | A61N 2/02 600/14 |
| 2003/0158585 | A1 * | 8/2003 | Burnett | A61N 1/36021 607/2 |
| 2004/0176805 | A1 * | 9/2004 | Whelan | A61N 1/40 607/2 |
| 2011/0263925 | A1 * | 10/2011 | Bratton | A61N 2/004 600/14 |
| 2012/0172653 | A1 * | 7/2012 | Chornenky | A61N 1/40 600/14 |
| 2013/0261374 | A1 | 10/2013 | Elder | |

FOREIGN PATENT DOCUMENTS

| | | | |
|---|---|---|---|
| EP | 0957987 A1 | 11/1999 | |
| WO | 89/05673 A1 | 6/1989 | |
| WO | 96/32158 A1 | 10/1996 | |
| WO | WO 2004011091 A1 * | 2/2004 | ............... A61N 1/32 |

OTHER PUBLICATIONS

Written Opinion of the International Searching Authority in PCT/GB2015/051102.

* cited by examiner

THERAPEUTIC FIELD GENERATOR DEVICE AND METHOD

FIELD OF THE INVENTION

This invention relates to a generator, particularly a generator to generate a low power electric field. The invention is particularly, but not exclusively, concerned with generators adapted to be portable, self-contained units, including units to generate low frequency electric or electromagnetic fields designed to have a therapeutic effect on people or animals.

SUMMARY OF THE PRIOR ART

The generation of low power electromagnetic fields is common in the field of short distance data and audio communication modules incorporated in many electronic devices. Bluetooth™ wireless technology is one such technology that exchanges data over short distances using short-wavelength UHF radio waves in the unlicensed industrial, scientific and medical (ISM) band between 2.4 GHz and 2.485 GHz. Such modules operate on low power, and typically make use of a small lithium battery cell as a power supply.

Commercialized devices intended to generate electromagnetic fields to produce a therapeutic effect operate at higher power levels and, where battery operated, generally require a 9-volt battery. The development of such devices has reflected a belief in the therapeutic value of magnetic fields, including pulsed electromagnetic fields (see for example US20130261374A1) Generally, developers and manufacturers have been concerned with creating strong magnetic fields, in so far as commensurate with an underlying understanding of the potential hazards associated with exposure to electromagnetic radiation.

Concerning the strength of the magnetic field, US20130261374A1 states that the device is arranged to generate a pulsed and varying electro-magnetic field having a peak amplitude in the region of one Gauss (1G) to 100G, and preferably between 10G and 50G, i.e. 1000 microtesla ($\mu$T) to 5000 $\mu$T. US20110263925 claims a device capable of creating magnetic fields up to 55G at a distance of two millimeters (mm) from the coil surface.

Examples of devices for generating low power low frequency electric or electromagnetic fields designed to have a therapeutic effect on people or animals can be found in EP0390844 and EP0957987. These relate to devices offering relief for conditions such as migraine, hypertension, lower back pain, premenstrual tension and ME, depending upon the frequencies stimulated. The devices of these inventions have to be on the skin or in very close proximity to the skin in order to produce an effect. This is not always convenient or comfortable. A further problem is that the generating means—coils in EP0390844 and a simple inflexible printed antenna in EP0957987—have to be encased in a hard protective covering in order to prevent breakage during device use.

The devices described in EP0390844 and EP0957987 are not effective in some people. This could be because the electromagnetic waves generated do not stimulate desired electrical activity in the user.

In EP0957987, a first and second signals are generated and output as an electromagnetic or electric field. The first signal is dependent on the detected frequency of the wearer's heartbeat, whereas the second signal is a train of pulses each having a width substantially equal to the width of a neuron depolarisation pulse of typically about 125 microseconds ($\mu$s). Regardless, the devices produced in accordance with EP0957987 were found to be not effective in some people.

SUMMARY OF INVENTION

In a first aspect of the invention there is provided an electromagnetic field generator device comprising: a field generating circuit containing at least one electromagnetic radiating element having a conductive track geometry in which adjacent tracks conduct electrical current in opposite directions such that, for a relatively large electric field arising in the radiating element, component parts of a magnetic field produced by the radiating element at least partially cancel each other out thereby to reduce an overall magnetic field associated with the relatively large electric field; a processor responsive to a control algorithm stored in memory, the processor configured to provide a control signal to the field generating circuit to cause the radiating element to generate: i) a base heartbeat reference; and ii) at periodic times, supplementing the base heartbeat reference with mutually exclusively generated frequency components below 500 Hz, preferably below 200 Hz and most preferably in the range of about 0.5 Hz to 20 Hz.

According to another aspect of the present invention there is provided a computer program product that, when run by a processor, enables the processor to execute procedure to generate a control signal having: a base heartbeat reference having a duration approximating that of neuron depolarization pulses; and at periodic times, to supplement the base heartbeat reference with mutually exclusively generated frequency components that correspond to one or more of: i) at least alpha brainwave frequencies; and ii) a succession of alpha brainwave frequencies followed by theta brainwave frequencies followed by delta brainwave frequencies.

In a further aspect of the invention there is provided a method of inducing a state or sleep or relaxation, the method comprising: generating an electromagnetic field from a radiating element, the electromagnetic field assembled from an electric field component and a magnetic field component, the electric field component having field strength of between about 200V/m and 3000V/m across a multiplicity of conductors configured as a radiating element having a pattern in which adjacent conductors have contra-flowing currents and wherein the magnetic field component is less than about 50 mT, preferably less than about 10 mT, more preferably less than about 1 mT and most preferably about 8 $\mu$T-10 $\mu$T as measured at the surface of the radiating element; and generating a base heartbeat reference; and at periodic times, supplementing the base heartbeat reference with mutually exclusively generated frequency components below 500 Hz.

Without wishing to be bound by theory, the inventors have surprisingly concluded that acceptability of incident electromagnetic waves at therapeutically useful frequencies is improved when the power of the magnetic field is reduced. In other words, contrary to the belief in the therapeutic value of magnetic fields, it is the electrical current induced by pulsed electromagnetic fields which may be therapeutic. The product of this invention overcomes the problem of lack of acceptability by reducing the magnetic field generated in a low power device whilst preserving or largely preserving the strength of the electric current.

The preferred embodiment produces a low power electric signal which can be used away from the body and can have a therapeutic effect on the body. It is desired to keep power levels extremely low both in the interest of user safety and to maximize battery life and efficiency, and also to keep the magnetic component as low as possible, whilst creating an electrical current sufficient to affect the body. This has been achieved by using a specially developed inductor which may be realized by printing a trace on a flexible circuit board—although it may alternatively by a trace on a convention PCB or a coil around a core—to mitigate the risk of its breakage during use. Using this inductor it is possible to create larger electric fields than those produced by the products claimed by EP0390844 and EP0957987 so that devices incorporating the inductor/conductor configuration can produce a beneficial therapeutic effect without being in direct or very close contact with the user. Devices incorporating the principles of the preferred embodiments may, for example, be placed under a pillow without negating their effects. They are able to withstand a certain amount of movement and are easier and less expensive to produce than the devices described in EP0390844 and EP0957987.

The problem of limited efficacy has been overcome by the design of and use of a new inductor in the circuit of the wave generator of the present invention. The specially developed printed inductor has been designed to minimise the strength and size (flux density) of the magnetic field generated by the electric current that is passed through the printed circuit.

An electric current, or changing electric field, will generate a magnetic field; this follows from Ampere's law of electromagnetism, as modified by Maxwell. Antennae may be designed to affect the quality of a field so, for example, equipment can be designed using toroidal antennae which minimise magnetic interference by concentrating the magnetic field (generated by the current flowing through the antenna) in the centre of the toroid.

We have developed a radiating element (within a therapeutic wave generating device) in which part of the magnetic field—generated by the changing electric field through the of our wave generator of the radiating element—is effectively cancelled, whilst an electric current of sufficient strength to affect the body is maintained. The preferred embodiment does not prevent the generation of the magnetic field, but rather inhibits its size by cancelling out parts of the magnetic field to reduce field intensity such that a smaller magnetic field is radiated and the user consequently exposed to a reduced magnetic field.

The present invention provides an electric or electromagnetic field generator comprising transmitting/output means, i.e. a radiating antenna or element, in which each of the lines of current are adjacent or close to one or two lines designed to conduct current in the opposite direction such that, in use, part of the magnetic field which would otherwise exist is cancelled. The field generator apparatus is adapted to generate two trains of pulses simultaneously: the first train of pulses consisting of one or more frequencies within the normal range of the frequency of the heartbeat, and the second train of pulses consisting of one or more frequencies within a frequency range known to produce a desired effect in the body or otherwise identified as missing or weak in the user whether by reason of disease, deficiency or injury.

In a preferred embodiment of the invention the transmitting/output means is a printed inductor on which each of the lines of the printed circuit are adjacent or close to one or two lines which conduct current in the opposite direction. Thus, the magnetic fields created by the electric current as it flows through each line of the printed circuit overlap one and two opposing magnetic fields are created by the flow of current in the opposite direction The opposing magnetic fields act to cancel each other (at least to some extent and generally an appreciable extent). The cancelation of magnetic fields may not occur or may be reduced at areas in the radiating antenna where the adjacent lines of current changes direction, such as at an end radii or corner. The electric current is not cancelled, although the reduction in magnetic field may affect the power of the electric current.

The effectiveness of this invention may be evaluated by reference to Bluetooth modules, which are of similar low power to the products of this invention, and also generate low power electromagnetic fields. The magnetic field produced by a typical Bluetooth module is around 800 milliteslas (mT). This may be compared with a typical product of this invention in which the electric field is between about 200 volts per meter (V/m) to about 3,000 V/m and the magnetic field produced is below about 300 mT (milliteslas), and typically much lower. Preferably, the magnetic field is less than about 50 mT, generally less than about 10 mT and more preferably below about 1 mT and most preferably about eight microteslas to ten microteslas (8 µT-10 µT) or below as measured on/at (or very close to) the surface of the radiating antenna/inductor.

Electromagnetic or electric fields generated in the manner of this invention have a higher rate of acceptance by the human body, as measured by more widespread therapeutic effects, and may achieve better results in stimulating electrical activity in the brain or body. They also have a larger electrical field. We can increase the field size and the range in which devices have a therapeutic effect by increasing the number of windings on the printed circuit. By using this method, it is possible to achieve therapeutic effects at lower power than is possible using other methods. This may maximise safety (it is generally accepted that lower power correlates with great safety) and means that small batteries can be used, and battery life prolonged so that recharging (where rechargeable batteries are used) is minimised.

The limitations of printed circuit technology mean that this approach is restricted to low power, low voltage applications. Currently, printed inductors are used in applications requiring the generation of milliwatts (mW) of power or less. Such inductors can be used to produce very low frequencies up to radio frequencies. The present invention could be used with the full range of frequencies that can be produced by printed inductors, up to a voltage level of around 5 Volts (V). The use of silicone chip technology could further increase the power and frequency levels which could be generated. Similar effects could be achieved using pre-digital technology (coils and wound antennae), but these would require greater power.

When used for therapeutic purposes, frequencies within the range generated by the human body are useful, and printed inductors or the like are typically adapted to generate one or more frequencies in the range of about 0.5 Hertz (Hz) to about 400 Hz. For therapeutic use, devices are adapted to generate frequency (ies) in the delta range similar or equal to the heart rate of the user (generally around 1.15 Hz to 1.2 Hz) together with frequency (ies) which have been identified as useful to produce a desired effect.

Typically, the electric or electromagnetic field generator means comprises a microcontroller connected to the inductor. The microprocessor comprises memory, preferably, and stores values representative of the different frequencies of a pulse train. The memory preferably holds a sequence of values in the range of about 0.5 to 10 Hz, and the microcontroller accesses the memory sequentially acquiring the values in turn so that the frequency of the signal pulse train is changed depending on the required value.

A portable therapeutic field generator device of the preferred embodiment therefore generates a reduced magnetic field component for a relatively large electric field by virtue that adjacent conductive tracks in a radiating element conduct electrical current in opposing directions. The device includes a processor that, in response to a control algorithm stored in memory, supplies a pulse wave to a circuit containing the radiating element. The pulse establishes generation of a base heartbeat reference having a frequency around a nominal heart rate. At periodic times, the base heart beat reference is supplemented by mutually exclusive periods of alpha waves, theta waves and delta waves generation based on selected brainwave frequencies for these waves, with the pulses having a duration generally corresponding to that ascribed to neuron depolarisation pulses. The device cycles through multiple operating cycles in which delta waves follow theta waves that follow alpha waves, with each of these waves at a selected frequency groups of frequencies. Delays may exist between transitions between the generated waves, with delta wave generation occurring no later than about one hundred minutes from commencement of alpha wave production. Delta waves production has, typically, a duration that is twice that of either the alpha or theta wave production.

The device's configuration and operation may, for example, offset undesirable aspects of conditions such as narcolepsy, i.e. a sleep disorder which affects the brains ability to regulate the normal sleep-wake cycle, amongst others.

The reduced magnetic field from the antenna layout is applicable for reinforcing and/or supplementing brainwave frequencies and also for muscle group stimulation.

DESCRIPTION OF THE FIGURES

The above and other aspects of the present invention will now be described, by way of example only, with reference to the accompanying drawings in which.

DESCRIPTION OF A PREFERRED EMBODIMENT

Figure 1:
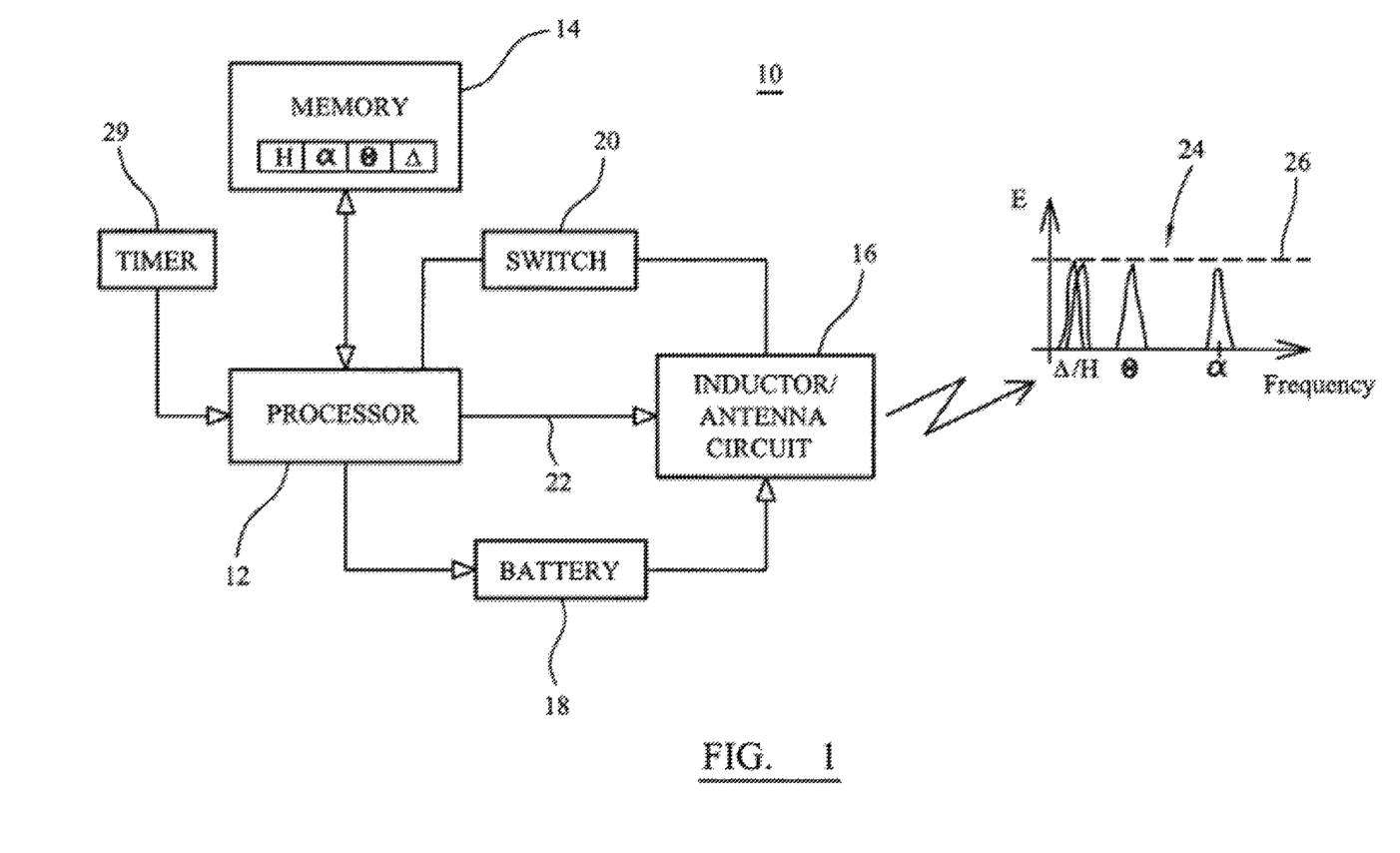
FIG. 1 is a block diagram showing the main features of a wave generator of a therapeutic field generator device in accordance with the present invention.

Referring now to FIG. 1, an embodiment of a therapeutic field generator device 10 includes an electric or electromagnetic field generator in accordance with the present invention. The therapeutic field generator device 10 has a control processor 12, such as a microcontroller, having an input/output connected to a memory 14. An output of the processor 12 is connected to a wave generating circuit 16 that includes an inductor/conductive trace (see FIGS. 2 and 3) that realizes a short range, electromagnetic radiating antenna. A battery 18 provides power to the processor 12 and the wave generating circuit 16. A switch 20, coupled to the processor 12, operates to regulate power and an On-Off state to the therapeutic field generator device 10, or otherwise provides a reset function for wave control instructions communicated from the processor (in accordance with instructions stored in the memory 14) to the wave generating circuit.

The therapeutic field generator device 10 may include, optionally, some form of display indicating a current status of the device in terms of an operational On-Off state of the device and/or the nature of the frequency of waves being generated.

The memory 14 stores a program that permits the controlled generation of different waves having different frequency. More specifically, the memory 14 stores a number of program modules that relate to one or more of: (i) heart rate (H); ii) alpha (A, α) brainwave patterns; iii) theta (Q, θ) brainwave patterns; iv) delta (Δ, δ) brainwave patterns; and other frequencies that have identified effects on the brain and/or muscles, including (a) beta frequencies (in the range of about 12 Hz to about 38 Hz), (b) gamma frequencies (in the range of about 38 Hz to about 90 Hz), (c) hyper gamma frequencies around 100 Hz and lambda frequencies up to about 200 Hz as both apparently carried by the sub-0.5 Hz epsilon frequency, and (d) muscle stimulation frequencies up to around 500 Hz.

For operation in a particular sleep-inducing mode, the memory may therefore store code arranged to replicate nominal or mid-band frequencies for each of the heart rate and the α, θ and δ brainwave frequencies or a narrowband range of frequencies associated with one or more the heart rate and the α, θ and δ brainwave frequencies. In fact, therapeutic field generator device 10 may include a user interface that permits the entry of a user's heartbeat and/or selection of either a discrete brainwave frequency or a narrowband frequency range around a peak value for one or more of the α, θ and δ brainwave frequencies. Generation of discrete frequency components having a variation of better than +/−0.5 Hz are by their nature understood to be more targeted and have proven generally to have a higher level of efficacy.

In a particular relaxation-inducing embodiment, the memory only stores a heartbeat and an alpha (α) mid-range frequency (nominally around 10 Hz), since these in combination are found to have beneficial effects regardless of further complementary use of theta (θ) and delta (δ) frequencies. More specifically, the combination of a synchronization base heartbeat frequency and an alpha brainwave pattern, when played cyclically, are found to induce a state of relaxation. Whilst a synchronization heartbeat may always be present, alpha frequency generation and transmission may occur for bursts of between about ten and twenty minutes, with the duty cycle of between about 1:2 to 1:4 and preferably about 1:3, e.g. a ten minute burst following by twenty minutes of no alpha transmissions.

In general, the processor 12 reads a value for the heart rate and a selected one of the frequencies (e.g. the alpha, theta and delta frequency components for the sleep-inducing mode) from the memory 14 in order to generate a control signal 22 having the form of a train of regular pulses (or "pulse train"). Selection of the alpha, theta and delta frequency in the sleep-inducing mode is dependent upon the point reached within an overall cycle for the field generator device, with the cycle having two components: i) a total "sleep-inducing cycle" based, in one embodiment, on the four sleep phases/cycles experienced during normal human sleep; and ii) multiple contiguous operating cycles that make up an operational period. The pulse train causes the generation of a varying electric current in an inductor/conductive trace of the wave generating circuit 16 and therefore the production of an electromagnetic field having electric field and magnetic field components. From a frequency perspective, an output from the radiating antenna is shown as graph 24 of FIG. 1, with spectral bands provided around the nominal medium frequencies accepted for heartbeat (H) and delta, theta and alpha brainwaves.

As will be understood, delta waves are understood to have a frequency between about 0.5 Hz and 3 Hz, theta waves between about 3 Hz and 7 Hz and alpha waves between about 7 Hz and 12 Hz. The precise bands are source dependent, as will be understood. In terms of energy within each band, it is preferred that each spectral component (whether heartbeat or a brainwave) is substantially the same, although variations in levels over time or otherwise are not precluded. The generally constant level in energy is shown by the datum line 26 in FIG. 1.

Individual pulses for brainwave frequencies in the delta to lambda frequency range preferably resemble the general form of a neuron depolarization impulse, but may also take other suitable and effective forms such as square-wave and a wave forms with a sharp rise time and a relatively gradual tail-off/decline. For brainwave frequencies, each individual has a typical pulse width of between about 100 microseconds (100 µs/mu seconds) and about 145 µs and preferably has a width of 125 µs. The duty cycle to a frequency corresponding to the value obtained from memory for, say, a 1 Hz heart rate is therefore about 1 to 8000 (or 0.0125%). The pulse width is selected to mimic the naturally occurring neuron depolarization pulse width for brain signals.

For muscle stimulation processes, a typical pulse width will be between about 0.5 milliseconds (ms) and about 10 ms. As will be understood, the selected muscle stimulation frequency is dependent upon the muscle group that is to be target by the field generator device of this embodiment. With muscle stimulation, effective operational frequencies transmitted by the antenna are in the typical range of 100 Hz to about 500 Hz and more usually in the range of 200 Hz to about 450 Hz.

By way of intermediate recap on the sleep-inducing algorithm and process employed by a preferred embodiment, the data values stored in the memory 14 represent: i) a range of frequencies corresponding to the frequencies of normal heartbeats; ii) particular frequencies considered to produce a desired effect; and/or iii) particular frequencies identified as or believed to be missing or weak in the patient, whether missing or weak by reason of disease, deficiency or injury. The processor 12 accesses a frequency value and thereby causes a pulse train at that frequency to be generated, each pulse having a nominal duration of 125 µs.

The wave generating circuit 16 is arranged to provide a heartbeat frequency that provides a consistent base reference throughout an entire active phase for the device of FIG. 1. The active phase is made up from a plurality—preferably four—operation phases that share some common frequency burst characteristics. In a preferred embodiment each operating cycle (other than the first cycle) is nominally ninety minutes, although it is noted that sleep cycles (and therefore operating cycles) can actually last up to about one hundred and twenty minutes. The heartbeat base reference is preferably always present regardless of the presence or absence of an overlaid brainwave frequency in one of the alpha, theta, delta, beta, gamma and lambda ranges. In one particular embodiment, at points where there are no alpha, theta or delta frequency (and narrowband spectrum) present, then the heartbeat base reference may be suppressed, with the processor 12 operable to maintain timing and to re-introduce a mix of both the heartbeat base reference (interchangeable referred to as the "heartbeat base pulse") with one of the mutually exclusively applied alpha, theta or delta frequencies. By providing a heartbeat base reference, physiological synchronization between the emitted heartbeat base reference and the user's heartbeat is maintained and is believed to cause increased positive physiological acceptance of overlaid brainwave pulses delivered by the device 10 at the brainwave frequencies. As will be understood, unless fully monitored, the methodology employed by the device of the present invention may bring about a slight variation in frequency between the user's natural and instantaneous heartbeat and the heartbeat base reference produced by the device 10.

Figure 2:
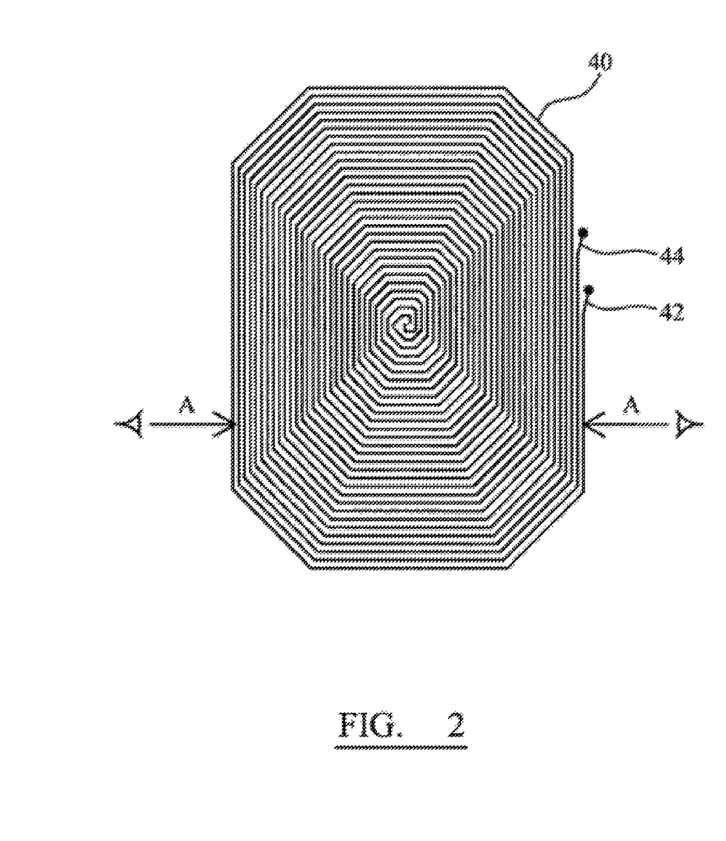
FIGS. 2 and 3 illustrate suitable forms of inductor for producing an electromagnetic/electric field in the therapeutic field generator device of FIG. 1.
Figure 3:
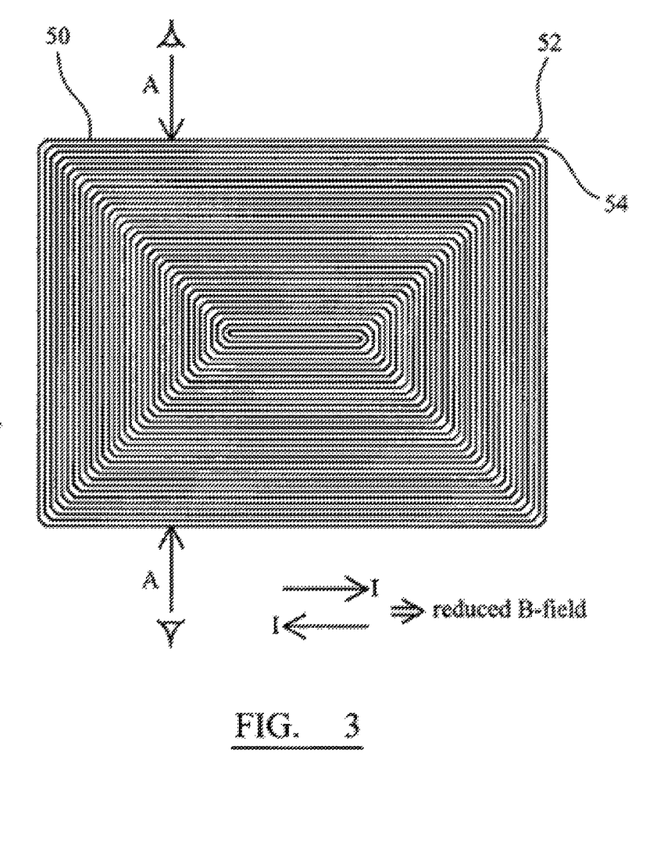

Referring to FIGS. 2 and 3, preferred geometries for a radiating antenna/inductor—driven by the pulse train by operation of the processor 12—are shown. In FIGS. 2 and 3, a suitable inductor 40, 50 is ideally etched in copper on the same printed circuit board as other components of the control circuit, including filters, transistors and ASICs. The radiating antenna/inductor 40, 50 includes closely located conductive traces or wires 42, 44 and 52, 54 that follow a generally spiraling path in a symmetrical layout, such as an octagonal shape (as in FIG. 2) or a rectangular shape (as shown in FIG. 3). The terms radiating element, antenna and conductive traces should be considered as being functionally synonymous since they are intended to describe a physical structure that passes current to induce an electromagnetic field having an electric field component and a magnetic field component.

As indicated above, the generator is preferably battery-powered, for example, by a lithium battery that offers relatively good performance and long life. The battery may be realized by alternative chemistries and may be of a rechargeable nature. Use of such a battery with the radiating antenna/inductor 40, 50 on the circuit board is designed to produce a field with an electric field strength of between about 100V/m to about 1,000 V/m and a magnetic field of less than about one microtesla (1 µT) at a distance of about thirty millimeters (i.e. 3 cm) from the antenna/radiating element 40, 50. The relatively low total magnetic field is consequential on the presence of counter-flowing electrical currents within close neighbouring or immediately adjacent copper tracks of the radiating antenna/inductor 40, 50. It is understood that the relative position, proximity and counter-current flow within such near-neighbouring conductors produces local magnetic field components that magnetically offset each other, i.e. they counter-balance each other on a local level, to reduce or "damp" the overall magnetic flux density from the circuit 16, whilst seeing a maintained electric field by the therapeutic field generator device 10. The physical consequence of the track layout is that, when viewing the radiating element/antenna 40, 50 in section A-A through the plane of the radiating antenna/inductor 40, 50 will see adjacent current pipes ⊙⊚⊙⊚⊙⊚, etc. having electrical charge flowing toward (⊙) or away from (⊚) from the viewer. Other trace layout geometries may be substituted, as will be understood, although magnetic field cancellation may be inferior to a layout providing direct, side-by-side contra-flowing currents. However, functionally, the positive effects of the device of the present invention are achieved with a relatively low magnetic field strength in the range of about 1 µT to 300 mT (and more usually in the range of less than about 10 mT) as measured at the surface of the antenna for an electric field in the range of about 200 V/m to 3000 V/m.

The use of a printed circuit, rather than coils in a toroid configuration, allows the therapeutic field generator device 10 to be encased in silicon or plastic, e.g. polyurethane or polyamide. In this manner, components cannot move, durability is improved and the risk of breakages is reduced. Manufacture can be readily computerised and costs reduced accordingly. The field generator device may include one or more radiating antenna or inductor, with a first inductor used for the base heartbeat reference and the second radiator used for production of brainwave frequency components. However, construction of a multiplexed pulse train from individual frequency components for the base heartbeat reference and the overlaid alpha, theta or delta component allows (in a preferred embodiment) use of a single radiating antenna 40, 50.

The device may be housed in flexible housing which may be fixed to a body of a user, for example, by means of a strap and therefore worn on the wrist, arm or leg. Otherwise the device may be incorporated in clothing, or placed under or within a pillow. In the case of an animal, the device may be incorporated within in a saddle or other equipment used close to the body of the animal.

Figure 4:
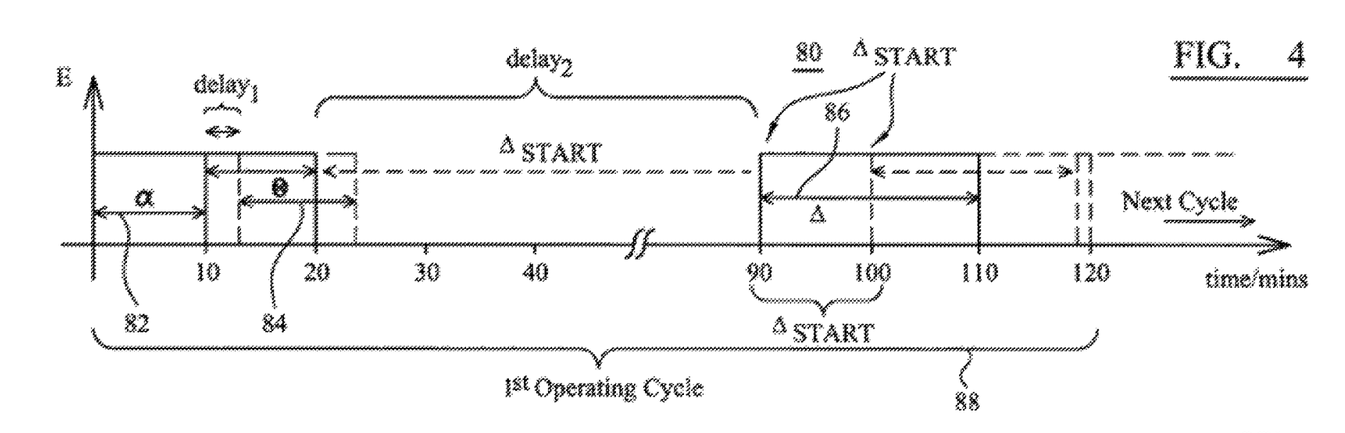
FIG. 4 is a time domain representation showing preferred relative timing between alpha, theta and delta waves generated by the therapeutic field generator device of FIG. 1.

Referring to FIG. 4, a time domain representation 80 shows preferred relative timing between alpha 82, theta 84 and delta 86 waves generated by the therapeutic field generator 10 device of FIG. 1, especially within the first operating cycle for the device. With the operating cycle 88 nominally set at between about ninety minutes and about one hundred and twenty minutes (bearing in mind that sleep cycles typically have a period of between about ninety minutes and two hours), the memory 14 stores a procedure that initiates the base heartbeat reference frequency ("$H_x$" in FIG. 5, where x is an integer having a pulse width $PW_2$) and simultaneously commences an overlaid, i.e. mixed, alpha frequency ("$α_x$" in FIG. 5, where x is an integer having a pulse width $PW_2$) for a duration of about ten minutes. The ten minute duration has been found to be sufficient to generate a mood of relaxation, but insufficient to induce irritation in the user incident to the generated fields.

Figure 5:
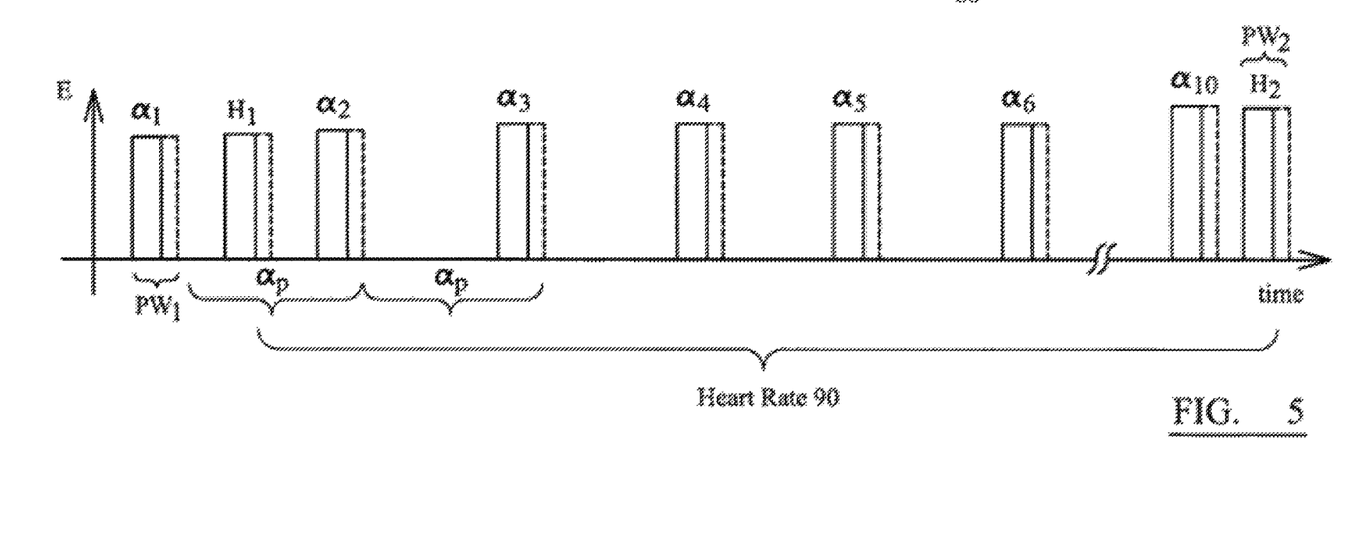
FIG. 5 is a time domain representation showing relative timing and relative pulse widths between nominal heart rate and exemplary alpha pulse generation, the time domain being exemplary of a preferred operating methodology.

Referring briefly to FIG. 5 is a time domain representation showing relative timing and relative pulse widths between nominal heart rate and exemplary alpha pulse generation, the time domain being exemplary of a preferred operating methodology. The pulse widths ($PW_1$) for the (exemplary) alpha frequency may be the same as the pulse width for the heart rate ($PW_2$), although this need not be the case, as reflected by the extended dotted lines for the pulses. As indicated above, each pulse width is between about 100 microseconds (100 μs/mu seconds) and about 145 μs and typically 125 μs. A relative period between the base heartbeat/heart rate reference 90 and the exemplary alpha period ("$α_p$) reflects the different frequencies.

Returning to FIG. 4, at the end of the ten minute alpha cycle, alpha wave production is stopped and theta wave production commenced. The switch from alpha to theta production can be near instantaneous, e.g. a few hundreds of microseconds to less than about ten seconds. However, there can be a longer induced delay ("delay 1" in FIG. 4) of up to about four minutes. This four minutes is considered the upper limit for transitional delay between operating modes of the field generator device of FIG. 1.

The generated theta frequency may be a discrete frequency or a narrowband theta band range. Production of theta waves (θ) 84 continues for about another ten minutes.

At the end of theta wave production, the processor—in following instructions in the computer program product loaded into memory device 14 of FIG. 1)—commences delta wave generation 86. Delta wave production can commence near instantaneously, e.g. about a few hundred microseconds, after the termination of the theta wave cycle, or otherwise can be delayed for a period of time (delay$_2$). The delay may, in fact, be as long as about forty to eighty minutes, but is typically between sixty minutes to seventy minutes. Delta wave production will last for a longer period of time than either alpha wave or theta wave production. Typically, delta wave production 86 at a selected discrete frequency or in a narrowband spectrum of delta wave frequencies will continue for about twenty minutes and, according to the present invention, is therefore at about double the duration of alpha or theta wave production. Given delta wave production, its production can start as soon as about twenty minutes from device start up, or otherwise as late as about one hundred minutes after starting device operation. The duration of delta wave production is driven by the sleep cycle and reflects that delta waves in the brain of a normal sleeper occur at fixed periods associated with deep sleep.

The field generator device 10 of FIG. 1 will therefore include some form of timer or clock (or equivalent software function) that regulates operation of the device and which, more specifically, controls timing for the generation of alpha, theta and delta frequencies.

Additionally, it is preferred that the device operates over four contiguous operating cycles that provide at least six hours of stimulation and preferably six and a half hours (i.e. three hundred and ninety minutes). Operational timing is set to enhance achievement of the natural sleep state. In fact, the field generator device of the preferred embodiments induces positive physiological benefits through the appropriate, timely and sequenced stimulation with appropriate frequencies in, especially, the range of about 0.5 Hz to 20 Hz and more particularly the range of about 0.5 Hz to about 12 Hz. The field generator device is therefore designed to produce the same frequencies as that of the relaxing and, preferably, the sleeping brain whilst preferably suppressing production of unnecessary, i.e. non-complementary or unwanted, frequency components.

As reflected in the time domain representations of FIGS. 4 and 5, transitions between different wave generating states mean that the next value in memory is accessed and a pulse or train of pulses at the new frequency is generated. In this way a series of pulses or pulse trains is generated to be combined alternately with the first (heartbeat dependent) signal and output as an electric or electromagnetic wave, each pulse or pulse train corresponding to a different value as stored in the memory 14. The memory 14 will also be programmed with other information, for instance the duration of each pulse train, which can be varied to expose the user to certain frequencies for longer.

Figure 6:
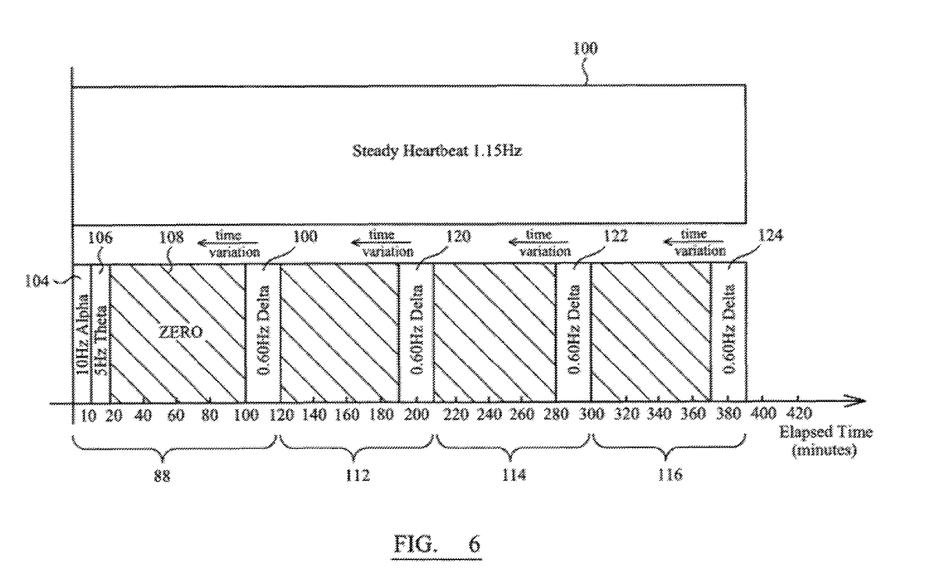
FIG. 6 is a timing diagram showing relative frequency generation during a preferred human sleep-inducing operational cycle of the therapeutic field generator device of FIG. 1.

It has been found that, for a sleep-inducing mode of operation and the use of alpha, theta and delta frequencies, an optimum relative timing is shown in FIG. 6. Specifically, a constant heartbeat base reference 100 at (nominally) 1.15 Hz (equivalent to 69 beats per minute) is generated and transmitted by the radiating antenna element 40, 50. At commencement of the first operating cycle 88, there are consecutive ten-minute bursts 104, 106 of alpha and theta frequencies. As indicated, there may be some slight timing separation between these two burst 104, 106 although they may be contiguous. A first sixty to eighty minute silence 108 then follows the theta transmission burst 106. A 0.6 Hz delta burst 110 is then generated and transmitted for about 20 minutes; this ends the first operating cycle 88 at no later than about one hundred and twenty minutes from commencement of the sleep-inducing first operating cycle. The subsequent second, third and fourth operating cycles each then preferably (and in the specific embodiment do) omit the alpha and theta bursts, so instead have just delta frequency bursts 112, 114, 116 spaced at about ninety minute intervals, with each delta frequency burst having a duration of about twenty minutes. This means that delta frequency bursts 120-124, in a preferred embodiment, commence at time points of 95±5 minutes, 185±5 minutes, 275±5 minutes and 365±5 minutes. The ±5 timing variation should be considered to be approximate and reflective of preferred practice for good efficacy. Delta frequency bursts in the second, third and fourth operating cycles 112-116 are therefore twenty minute bursts in every (preferred) ninety minute operating cycle, with the delta bursts inserted towards the end of each operating cycle.

It is noted that "sleep cycles", contrasted to operating cycles of the device of FIG. 1, are understood to typically run for between about ninety minutes and two hours in a healthy individual. FIG. 6 therefore shows the preferred embodiment with the majority of the operating cycles repeating at ninety minute intervals, with the first cycle 88 extended to include an initial relaxation-inducing period. It is contemplated that the preferred twenty minute delta frequency generation can occur within second, third and fourth operating cycles 112-116 that can be selectively adjusted or fixed at manufacture to have operating cycles of between about ninety minutes and two hours.

Duties between delta bursts and zero brain frequency output in the resting periods between burst can be as much as about 1:4, although something in the range of about 2:9 or 1:6 are more typical and preferred.

While not wishing to be bound by theory or conjecture, the natural variation in alpha frequencies in different people leant itself to implementing suppression of alpha frequencies after the first alpha burst 104 in the first sleep cycle 88. It is also understood that naturally occurring delta frequency variations are significantly less.

An alternative timing arrangement is entirely cyclic with identically set ninety minute operating modes, with alpha and theta frequency burst following on from (but timed delayed relative to) the delta burst. It has been found that it is preferably to leave silence between delta bursts. Again, the operating modes could be set to as long as two hours each, with ninety minutes being the preferred minimum timing for each operating cycle.

The term "cycle" and "mode", in the context of device operation, should be considered equivalent unless the specific embodiment and surrounding context requires a stricter interpretation, as will be understood.

Introduction of one or both of the alpha and theta frequencies following the end of the first operating cycle may be warranted, since it has been discovered that certain people with REM disturbances—manifested for example by nightmares—can benefit from additional limited duration theta frequency input in advance of each successive delta burst 120-124, whereas in others the introduction of additional theta bursts (in the second and subsequent operating cycles 112-116) may induce unnatural and therefore undesirable dream states into some individuals. To counteract this effect, in a certain very specific control algorithm and thus a very specific embodiment that does not follow conventional and natural sequences of brainwave generation during sleep patterns, a delta frequency burst may precede even the first alpha burst 104.

In general, the operating modes defined by code in the memory 14 (of FIG. 1) and executed by the processor generate a constant background heart rate reference (reference number 100 of FIG. 6 and $H_1$ and $H_2$ of FIG. 5), and then overlay periodically and discretely at least one other frequency (or narrowband frequency spectrum) related to either (i) a particular brainwave frequency, especially (but not limited to) alpha, theta or delta, or (ii) a muscle stimulation frequency.

In a preferred embodiment the battery 18 may be charged by placing the field generating device 10 on a charging pad; this enables the generator to be entirely encased in a suitable covering material, e.g. silicon, polyurethane, polyamide of other material so that the device is waterproof and risk of damage is reduced.

Preferred embodiments of the present invention provide a relaxation-inducing and sleep-inducing device which does not have to be next to or very close to the skin. The device of the preferred embodiment is therefore less obtrusive and less of an encumbrance than, for example, a device strapped to the wrist. The present invention also allows devices according to various embodiments to be used on animals easily, for example by incorporating them within a saddle or muzzle. Embodiments allow devices incorporating the timing methodology for field generation to be used under a pillow, for example, to assist sleep.

The generation of other brainwave frequencies for purposes other than trying to induce sleep or to promote relaxation are also considered and make use of the low magnetic field produced by the antenna/inductor 40, 50 of FIGS. 2 and 3.

The reduced magnetic field allows signals to be accepted by the body/brain and, consequently, the field generating device has the capacity to introduce or supplement missing brainwave frequencies that should or ideally are regularly or randomly generated by the brain. For example, the operating algorithm and device may together alleviate symptoms or effects associated with migraine, chronic fatigue syndrome ("CFS"), M.S., general pain, epilepsy and Parkinson's disease, since in many cases brain activity varies from the norm with these conditions.

Additionally, the generation of brainwave frequencies with limited magnetic fields can promote relaxation and potentially enhance creativity and concentration. As with sleep, we will introduce frequencies which should exist/ would be there in the absence of the condition/correlate with the state required.

Certain frequencies have been identified as being present during certain brain activities and artistic or intellectual activities. As already indicated, alpha waves are often present during relaxation, so a preferred selectable function of the field generating device generated alpha frequencies across the alpha range or otherwise as a limited spectrum. During periods of creativity, theta frequencies are present so a specific embodiment allows for selection and generation of these frequencies and related spectra. It is further contemplated that one embodiment may be able to select and generate beta frequencies that are often associated with periods of concentration.

Specific combinations of frequencies can also be generated by the device of the preferred embodiments to offset or treat symptoms. Durations for these frequencies are varied from a few minutes to tens of minutes, with the burst presented over a period of hours or continuously if desired. For example, algorithms may generate:

1. Alpha frequencies and one or more of alpha and delta frequencies for migraine relief.

2. Alpha frequencies or a combination of alpha and theta frequencies for MS management.
3. A combination of delta and theta and alpha and beta for CFS management.
4. For Parkinson's Disease, it is possible that gamma frequencies might be useful and an embodiment of the device of FIG. 1 programmed with a pulse train and bursts that produce local gamma frequencies to supplement or reinforce brainwave activities.

In each case, missing brainwave frequencies are, for example, empirically determined and the memory of the field generator device of FIG. 1 programmed with appropriate frequency components required to build a control pulse train. In fact, it is also noted that, in many cases, there are common elements for different people (e.g., a principal delta frequency of 0.6 Hz for inducing sleep appears to be common to most people), but in other cases individual determination may be required, e.g. through EEG monitoring. This precision is important to maximize efficacy across the population. By way of example, use a delta frequency of 0.6 Hz in the sleep-inducing operating state appears optimal, with a frequency of 0.5 Hz or 0.7 Hz not as effective.

The circuit may include separate radiating antennas for use in generating the base heartbeat reference and a selected one of the alpha, theta and delta brainwave frequencies. Preferably, however, a single radiating antenna provides a capacity to operate over a limited frequency spectrum between about 0.5 Hz and 200 Hz (and up to about 500 Hz for muscle stimulation embodiments), but at least between about 0.5 Hz and about 12 Hz. It is noted that certain frequencies in the beta (>12 Hz), gamma (38 Hz<γ<≈100 Hz) and lambda (~200 Hz) frequencies may also be produced by the apparatus of the present invention, with this antenna/inductor of FIGS. 2 and 3 (and the use of a complementary delivery frequency synchronized with the heart rate) permitting beneficial physiological effects to be experienced by the user of the field generator device 10.

For applications in specific animals, timing—and therefore the stored control parameters in the memory—within the sleep cycle is adjusted to reflect typically-experienced (and usually empirically-derived) transitions between different brainwave functions such that the field generator device induces positive physiological benefits through the appropriate, timely and sequenced stimulation of organs with appropriate frequencies in the range of about 0.5 Hz to 20 Hz and higher.

Also, since the production of a periodic alpha cycle mixed with just a base heartbeat reference has itself been found to induce a sense of relaxation, a preferred arrangement of the field generator device has an operating mode that just cycles through burst periods of alpha wave generation over a set period of time, e.g. between about ten minutes to about twenty minutes. Once the alpha wave generating period has elapsed, the device maintains low level production of the base heart rate references before recommencing with alpha wave generation after a predetermined delay of, typically, at least ten minutes and preferably between about thirty minutes and an hour.

Although many of the embodiments preferably always, i.e. at all active "on" times, generate and radiate a base heartbeat pulse, the use of the new antenna element 40, 50 having a reduced magnetic field can be used independently of the base heart rate pulse for the delivery of selected frequencies from the field generating device of the present invention. However, removal of the base heartbeat pulse is believed to inhibit the body's acceptance of and susceptiveness (in some of the population) to incident frequencies from the field device, especially brainwave frequencies below about 200 Hz and particularly below 38 Hz. Additionally, in certain embodiments, it is contemplated to shut down the base heart rate pulse in periods of zero complementary frequency transmissions and to recommence the transmissions either at the same time as, for example, the brainwave frequency is generated and transmitted or otherwise to commence the base heartbeat pulse shortly before the timed commencement of the brainwave frequencies. For example, the base heartbeat pulse might be started two to five minutes in advance of any scheduled complementary/supplementary delta frequency generation/transmission from the field generating device.

EXAMPLE

Sleep Inducement

A female patient of 65 years of age presented with chronic difficulties in her sleep pattern. Her sleep problems had begun with the menopause. The symptoms were frequent waking during the night, most nights, usually beginning after around 2 hours sleep and often a complete inability to sleep after around 4.30 a.m. This caused tiredness and irritability. The patient also suffered from persistent sinus trouble and chronic backache.

It was decided to program the field generator to produce frequencies in the alpha, theta and delta range in a pattern designed to emulate the pattern of the brain of a good sleeper, as well as a sequence of pulses within the range of frequencies corresponding to the range of frequencies of a normal heartbeat. The treatment was noticeably effective, with the effects being perceived from the first night of treatment and strengthening during a two week course of treatment, i.e. nightly access to the effects of the field generator device of FIG. 1. At the end of the trial period the patient reported much better sleep, generally waking no more than once each night, and quickly returned to sleep. She reported feeling much more relaxed during the day, with a considerable improvement in her energy levels and no sinus trouble or back ache during the period of use—factors which she attributed to the improved quality of her sleep.

Muscle Activation

The field generating device of FIG. 1 and the control algorithm in the memory 14 can be adapted to target operation or triggering of selective muscle groups. In this instance, as indicated above, the frequency pulse train will produce frequencies in the range of 100 Hz to about 500 Hz, and typically above 200 Hz. The pulse duration required for muscle stimulation is higher than that for brainwaves, with pulses arranged to have a duration of between about 0.5 millisecond (ms) and about 10 ms, and selected dependent generally upon the muscle or group of muscles to be stimulated and especially the size of the muscle. It is noted that muscle responses are not linear and that different muscle groups act in different ways and require different duty cycles. For smaller muscle stimulation, short duration pulse trains that produce stimulation frequencies of between about two minutes and about four minutes are effective. For larger groups, then frequency production from the device may be from about two minutes to twenty minutes. Cycling back to another burst of stimulation frequencies, if necessary, will typically occur in the once about every four to sixty minutes, with the duty cycle selected to permit the dissipation of lactic acid (or to avoid the build-up of relatively distressing levels of lactic acid in the targeted muscle). On-off duty cycles for muscles will therefore vary also from the perspective of the duration of the burst. For long bursts, the duty cycle between on-off states may be up to about 1:5. For short bursts, the duty cycle will typically be selected to be in the range of about 1:2 to about 1:4 and preferably about 1:3, i.e. 2 minutes on and four minutes off.

Again, with stimulation of muscle groups using the contra-flowing currents in the radiating antenna to reduce magnetic field size for a given electric filed, it is preferred to include a consistent synchronization base heartbeat pulse, as described above.

Those skilled in the art will further appreciate that the various illustrative logical blocks, modules, circuits, methods and algorithms described in connection with the examples disclosed herein may be implemented as electronic hardware, computer software, or combinations of both. To clearly illustrate this interchangeability of hardware and software, various illustrative components, blocks, modules, circuits, methods and algorithms have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

It will be further understood that unless features in the particular preferred embodiments are expressly identified as incompatible with one another or the surrounding context implies that they are mutually exclusive and not readily combinable in a complementary and/or supportive sense, the totality of this disclosure contemplates and envisions that specific features of those complementary embodiments can be selectively combined to provide one or more comprehensive, but slightly different, technical solutions.

It will, of course, be appreciated that the above description has been given by way of example only and that modifications in details may be made within the scope of the present invention. For example, while the device preferably makes use of a heartbeat frequency stored and reproduced from memory, the device of another embodiment may sense the user's actual heartbeat and then to generate a heartbeat signal that is more closely synchronized to the frequency and timing of the user's heartbeat. Sensing of the heartbeat may be achieved through incorporation of a suitable sensor in the device and may therefore include a wired sensor and/or a computer interface permitting entry of an empirically measured user heart rate. Of course, the inclusion of active monitoring or programmability increases complexity of the therapeutic wave generator device. Alternatively, heart rate data may simply be based on a sample period of, perhaps, thirty seconds instigated prior to device usage.

The invention claimed is:

1. A therapeutic electromagnetic field generator device comprising:
   a field generating circuit containing at least one electromagnetic radiating element having a conductive track geometry having a multiplicity of tracks in which multiple adjacent side-by-side pairings of tracks conduct electrical current in opposite directions configured such that, for a relatively large electric field arising in the radiating element, component parts of a magnetic field produced by the radiating element at least partially cancel each other out and reduce an overall magnetic field associated with the relatively large electric field;
   a processor responsive to a control algorithm stored in memory, the processor configured to provide a control signal to the field generating circuit to cause the radiating element to generate:
   i) a base heartbeat reference; and
   ii) at periodic times, supplementing the base heartbeat reference with mutually exclusively generated frequency components between 0.5 Hz and 500 Hz; and
   wherein the electric field across the radiating element is between 200 V/m and 3000 V/m and the magnetic field is between 1 uT and 300 mT as measured at the surface of the radiating element.

2. The electromagnetic field generator device according to claim 1, wherein the radiating element, responsive to a pulse train, generates mutually exclusively frequency components that correspond to a succession of alpha brainwave frequencies followed by theta brainwave frequencies followed by delta brainwave frequencies.

3. The electromagnetic field generator device according to claim 2, wherein the device operates in multiple cycles and a first cycle contains different frequency components to a successive cycle.

4. The electromagnetic field generator device according to claim 3, wherein the first cycle includes a first burst of alpha brainwave frequency, a first burst of theta brainwave frequency and a delayed first burst of delta brainwave frequency.

5. The electromagnetic field generator device according to claim 4, wherein a second cycle commences at an end of the time delayed first burst of delta brainwave frequency and the second cycle includes a second burst of delta brainwave frequency delayed in time relative to the end of the time delayed first burst of delta brainwave frequency.

6. The electromagnetic field generator device of claim 2, wherein the alpha brainwave frequencies, theta brainwave frequencies and delta brainwave frequencies each have a duration similar to the base heartbeat reference.

7. The electromagnetic field generator device of claim 2, wherein the delta brainwave frequency generation occurs for a longer period of time than alpha brainwave frequency generation.

8. The electromagnetic field generator device of claim 1, wherein the memory is configured to store a sequence of frequency values from 0.5 Hz to 12 Hz, and the processor is configured to access the memory sequentially to acquire stored frequency values and to generate the control signal in the form of a pulse train.

9. The electromagnetic field generator device as claimed in claim 1, wherein the magnetic field is between 1 μT and 50 mT, as measured at the surface of the radiating antenna/inductor.

10. The electromagnetic field generator device as claimed in claim 1, wherein the device is further configured to generate one or more frequencies in the beta range of between 12 Hz and 25 Hz.

11. The electromagnetic field generator device as claimed in claim 1, wherein the device is further configured to generate one or more frequencies in the gamma range of between 25 Hz to 100 Hz.

12. The electromagnetic field generator device as claimed in claim 1, wherein the device is further configured to generate one or more frequencies between 200 Hz and 400 Hz.

13. The electromagnetic field generator apparatus as claimed in claim 1, wherein the width of each brainwave pulse in a frequency range of 0.5 Hz to 200 Hz is between 100 microseconds and 145 microseconds.

14. A method of inducing a state of sleep of relaxation in a patient, the method comprising:
  generating and treating the patient with an electromagnetic field from a radiating element, the electromagnetic field assembled from an electric field component and a magnetic field component, the electric field component having field strength of between 200 V/m and 3000 V/m across a multiplicity of conductors configured as a radiating element having a pattern in which adjacent conductors have contra-flowing currents and wherein the magnetic field component between 1 µT and 50 mT, as measured at the surface of the radiating element; and
  generating a base heartbeat reference; and
  at periodic times, supplementing the base heartbeat reference with mutually exclusively generated frequency components between 0.5 Hz and 500 Hz, inducing the state of sleep or relaxation in the patient.

15. The method of claim 14, wherein the mutually exclusively generated frequency components are brainwave frequencies in the range of 0.5 Hz to 200 Hz, the brainwave frequencies produced in response to a pulse train in which each pulse has a duration of a neuron depolarization pulse.

* * * * *